US008268888B2

(12) United States Patent
Samnick

(10) Patent No.: US 8,268,888 B2
(45) Date of Patent: Sep. 18, 2012

(54) THERAPY OF MALIGNANT NEOPLASIAS

(76) Inventor: Samuel Samnick, Homburg/Saar (DE)

( * ) Notice: Subject to any disclaimer, the term of this patent is extended or adjusted under 35 U.S.C. 154(b) by 640 days.

(21) Appl. No.: 12/085,405

(22) PCT Filed: Nov. 27, 2006

(86) PCT No.: PCT/EP2006/011367
§ 371 (c)(1),
(2), (4) Date: Feb. 17, 2009

(87) PCT Pub. No.: WO2007/060011
PCT Pub. Date: May 31, 2007

(65) Prior Publication Data
US 2010/0003268 A1 Jan. 7, 2010

(30) Foreign Application Priority Data
Nov. 25, 2005 (EP) ..................................... 05025776

(51) Int. Cl.
*A61K 39/00* (2006.01)
*A61K 31/198* (2006.01)
(52) U.S. Cl. .................................... 514/567; 424/184.1
(58) Field of Classification Search .................. 514/567; 424/184.1
See application file for complete search history.

(56) References Cited

U.S. PATENT DOCUMENTS
5,816,999 A * 10/1998 Bischoff et al. .................... 600/3
2004/0131543 A1* 7/2004 Wong et al. .................. 424/1.11

OTHER PUBLICATIONS

Romeike et al. http://ar.iiarjournals.org/content (2004, abstract only, 2 pages).*
Zips (in vivo 19:1-8 (2005).*
Gura (Science, v278, 1997, pp. 1041-1042).*
Macfarlane et al Eur J Nucl Med (1996) 23:131-140.*
Goldenberg Current Oncology 14(1), 39-42.*
Tubis et al (Int. J. Applied Radiation and Isotope (1964), 15,397-400.*
Lawson (Introduction to Radioactivity (1999)1-20).*
Holoye et al. Chest 67, (6) 1975, 675-679.*
Romeike et al. Anticancer Research 24: 3971-3976.*
Fukushima,, et al., "Anti Tumor Activity of Amino-Acid Derivatives in the Primary Screening," *GANN* 66:29-36 (1975).
Hellwig, et al., "Validation of Brain Tumour Imaging With P-[1231]Iodo-L-Phenylalanine and Spect," *European Journal of Nuclear Medicine and Molecular Imaging* 32:1041-1049 (2005).
Kelly, et al. "Effects of P Chlorophenyl Alanine on Amino-Acid Uptake and Protein Synthesis in Mouse Neuro Blastoma Cells," *Biochemical Journal* 174:931-932 (1978).
Loeffler, et al., "Antineoplastic Agents: Structure-Activity Studies on N-Protected Vinyl, 1,2-Dibromoethyl, and Cyanomethyl Esters of Several Amino Acids," *Journal of Medicinal Chemistry* 20:1584-1588 (1977).
Meyer, et al., "Iodine-123-Labeled P Iodophenylalanine a Potential New Spect-Radiopharmaceutical for Brain Tumor Analysis," *Journal of Nuclear Medicine* 31:899 (1990).
Otani, et al., "M Halo Benzoyl and P Halo Benzoyl Derivatives of P Halo-D L Phenyl Alanine as Inhibitors in a Microbial Anti Tumor Pre Screen," *Research Communications in Chemical Pathology and Pharmacology* 40:325-328 (1983).
Otani, et al., "Structure Activity Relationships Among Substituted N Benzoyl Derivatives of Phenyl Alanine and its Analogs in a Microbial Anti Tumor Pre Screen.: Derivatives of M Fluoro-D L-Phenyl Alanine," *Research Communications in Chemical Pathology and Pharmacology* 40:321-324 (1983).
Baum, et al., "Systemic Endoradiotherapy With Carrier-Added 4-[$^{131}$I] Iodo-L-Phenylalanine: Clinical Proof-Of-Principle in Refractory Glioma," *Nucl Med Mol Imaging* 45(4):299-307 (2011).
Samnick, et al., "Efficacy of Systemic Radionuclide Therapy With P-131I-Iodo-L-Phenylalanine Combined With External Beam Photon Irradiation in Treating Malignant Gliomas," *J of Nucl Med* 50(12):2025-32 (2009).

* cited by examiner

*Primary Examiner* — Brandon Fetterolf
*Assistant Examiner* — Shirley V Gembeh
(74) *Attorney, Agent, or Firm* — Dahna S. Pasternak; Pasternak Patent Law

(57) ABSTRACT

The present invention provides a 3-iodo-L-phenylalanine or 4-iodo-L-phenylalanine for the preparation of a pharmaceutical composition for the treatment of malignant neoplasia. Moreover, the invention provides a method for the treatment of malignant neoplasia, the method comprising the steps of administering 3-iodo-L-phenylalanine or 4-iodo-L-phenylalanine to a subject in need thereof and a pharmaceutical composition comprising 3-iodo-L-phenylalanine or 4-iodo-L-phenylalanine.

16 Claims, 8 Drawing Sheets

THERAPY OF MALIGNANT NEOPLASIAS

CROSS-REFERENCE TO RELATED APPLICATIONS

Figure 1:
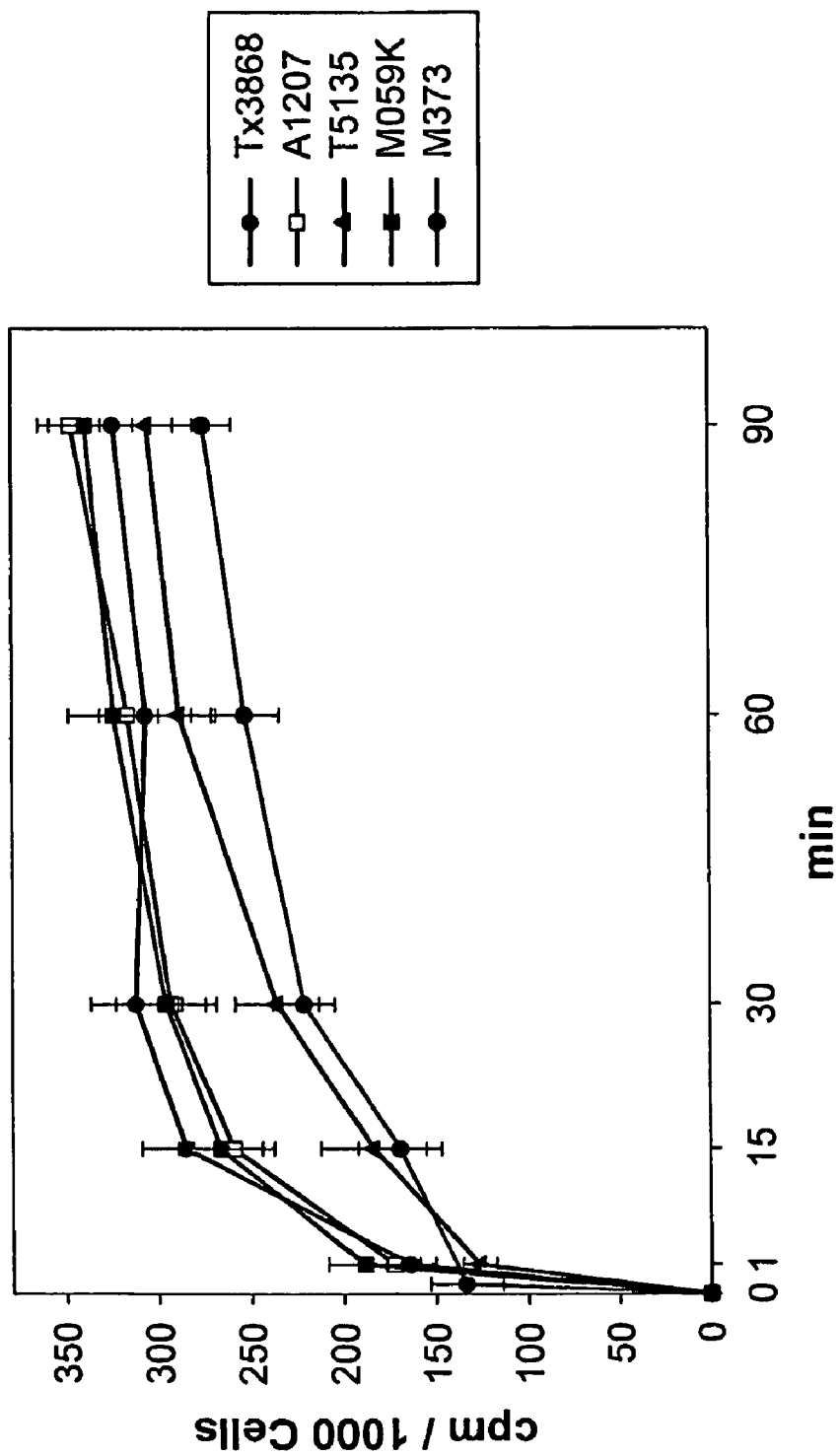

This application is a 35 U.S.C. §371 filing of PCT/EP2006/011367, filed Nov. 27, 2006. PCT/EP2006/011367 claims the benefit of European Patent Application No. 05025776.5, filed Nov. 25, 2005. The disclosures of the aforementioned applications are incorporated by reference in their entireties for all purposes.

The present invention provides a 3-iodo-L-phenylalanine or 4-iodo-L-phenylalanine for the preparation of a pharmaceutical composition for the treatment of malignant neoplasia. Moreover, the invention provides a method for the treatment of malignant neoplasia, the method comprising the steps of administering 3-iodo-L-phenylalanine or 4-iodo-L-phenylalanine to a subject in need thereof and a pharmaceutical composition comprising 3-iodo-L-phenylalanine or 4-iodo-L-phenylalanine.

A variety of documents is cited throughout this specification. The disclosure content of said documents including manufacturer's manuals is herewith incorporated by reference in its entirety.

Advanced malignant neoplasias are characterized by a locally infiltrative disease and the formation of one or multiple microscopic or macroscopic local or distant metastases. It is known in the art for such neoplasias that a concomitant phenomenon is the development of resistance to conventional chemotherapy regimens. Examples are recurrent malignant glioma, advanced breast cancer, advanced ovarian cancer, advanced prostate cancer, advanced malignant melanoma, or multiple myeloma. These neoplasias are typically not amenable to curative local treatment, such as e.g. surgery or local radiation therapy, but instead require the systemic administration of therapeutic agents, typically chemotherapeutic regimens. Even the use of chemotherapeutics, containing a combination of different agents in order to impede the development of chemoresistance to single agents and to optimize the tolerability of the usually highly toxic regimens to patients fails in a significant number of cases.

Established first line chemotherapy regimens for advanced neoplasias induce in some tumor entities complete remission rates of up to 10-20% [1-2]. In contrast, the response rates of repeatedly recurrent disease are much lower due to the development of inducible chemoresistance or selection of chemoresistant mutants. Other tumors, such as malignant gliomas are primarily resistant to most chemotherapeutic agents, due to either pharmacokinetics (e.g. no penetrance of the blood brain barrier) or intrinsic chemoresistance. Diminished chemosensitivity may be mediated by inducible cellular detoxicification mechanisms, such as PgP, MDR gene products and others.

Chemotherapy regimens used to treat advanced stage cancers include second line alkylating agents such as melphalan, platinum-containing compounds, topoisomerase inhibitors, or antimetabolites, are associated with extremely toxic effects on bone marrow and other organs, limiting therapeutic or palliative administration [3-5].

It is known that most tumors share the ability to accumulate amino acids more effectively than normal tissues and non-tumoral tissue with pathologies, such as e.g. inflammatory diseases. Therefore, radiolabeled amino acids have been used to image tumors clinically, using nuclear medical techniques such like positron emission tomography and single photon emission computed tomography [6]. 4-Iodo-L-phenylalanine (IPA) is a iodinated naturally occurring amino acid, which exhibits a high affinity for human tumors. Its marked accumulation in tumor is primarily associated with the increased amino acid transport into the neoplastic cell, which has been shown to be specific for many tumors [7]. Initial clinical evaluation with the iodine-123 labeled analogue 4-[$^{123}$I]iodo-L-phenylalanine (IPA-123) demonstrated the effectiveness and safety of single photon emission tomography (SPET) with IPA-123 for brain tumour imaging [8, 9]. IPA-123 crosses according to [8, 9] the blood-brain barrier after intravenous administration and accumulates specifically in malignant gliomas with prolonged retention in tumor.

A series of amino acid derivatives have been tested for their antineoplastic activities in antitumor screens [10-15]. They include the halobenzoyl-DL-phenylalanines, N-chloroacetyl derivatives of para-substituted phenylalanines, N-benzoyl-fluorophenylalanine, p-chloro-DL-phenylalanine, a-methyl-phenylalanine, N-ethylcarb-aminomethyl-L-isoleicine and N-propionyl-L-valine, to name only some. However, the administration of all compounds from said group is also known to be associated with extremely toxic side effects on bone marrow and other organs, limiting therapeutic or palliative administration. For example it has been known the art since 1974 that p-chlorophenylalanine interferes with the growth of developing rats [16] which disqualifies this class of compounds as a potential compound for the treatment of malignant diseases with an acceptable toxicity profile. Moreover, the effective doses of the compounds described in the corresponding document was relatively high. For example, in [15] it was described that a dose of 2.5 to 10 mmol/l of p-chloro-phenylalanine(4-chloro-phenylalanine) was necessary to demonstrate a cytotoxic effect of the compound on murine neuroblasts.

Thus, the technical problem underlying the present invention is to provide means and methods for an improved treatment of malignant neoplasias. The solution to this technical problem is achieved by the embodiments characterized in the claims.

Accordingly, the present invention relates to a use of 3-iodo-L-phenylalanine or 4-iodo-L-phenylalanine for the preparation of a pharmaceutical composition for the treatment of malignant neoplasia.

Iodo-L-phenylalanine in the forms applicable in accordance with the present invention are presented by the general formula I:

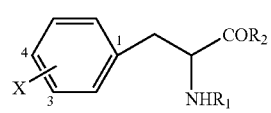

General formula I

In which,

X is an iodine linked to L-phenylalanine at the 3- (meta-) or the 4- (para-) position within the aromatic ring.

$R_1$ is H, alkyl group, amino acid, peptide, protein or other residues known to facilitate or improve tumor targeting.

$R_2$ is OH, amino acid, or other residues known to facilitate or improve tumor targeting.

The 3-iodo-L-phenylalanine may also be designated meta-iodo-L-phenylalanine (IMA) and the 4-iodo-L-phenylalanine as para-iodo-L-phenylalanine (IPA).

It is preferred that $R_1$ is H and $R_2$ is OH. It is moreover preferred that the iodine conjugated to the L-phenylalanine is the stable, non-radioactive [$^{127}$I]-iodine isotope.

The term "malignant neoplasia" describes in the context of the present invention a cancer, carcinoma, sarcoma, or other tumor, characterised by progressive, uncontrolled, invasive and or metastatic growth. A malignant neoplasia leads invariably to death if not treated.

An indication for the administration of a pharmaceutical composition comprising 3-iodo-L-phenylalanine or 4-iodo-L-phenylalanine to a subject with malignant neoplasia is also the diagnosis of minimal residual disease, preferably an early solid tumor, advanced solid tumor or metastatic solid tumor, which is characterized by the local and non-local recurrence of the tumor caused by the survival of single cells.

In accordance with this invention, the term "pharmaceutical composition" relates to a composition for administration to a subject, preferably a human patient. The pharmaceutical composition is preferably administered orally, parenterally, transdermally, intraluminally, intra-arterially, intrathecally or intravenously. Also preferred is a direct injection of the pharmaceutical composition into malignant tissue. It is in particular envisaged that said pharmaceutical composition is administered to a patient via infusion or injection, or as a tablet or capsule. Administration of the suitable compositions may be effected by different ways, e.g., by intravenous, subcutaneous, intraperitoneal, intramuscular, topical or intradermal administration. The pharmaceutical composition may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Preferred dosages for the administration of the 3-iodo-L-phenylalanine or 4-iodo-L-phenylalanine are described herein below. The compositions may be administered locally or systemically. Administration will generally be parenteral, e.g., intravenous, or oral. In an preferred embodiment, the pharmaceutical composition is administered subcutaneously and in an even more preferred embodiment intravenously. In another preferred embodiment, the pharmaceutical composition is administered orally. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition might comprise proteinaceous carriers, like, e.g., serum albumin or immunoglobulin, preferably of human origin. It is envisaged that the pharmaceutical composition might comprise, in addition to 3-iodo-L-phenylalanine or 4-iodo-L-phenylalanine further biologically active agents, depending on the intended use of the pharmaceutical composition in a treatment comprising the administration of additional agents for a concomitant therapy. Examples for such further biologically active agents are described herein below in the context of uses and methods comprising a concomitant therapy.

No pharmacological effect such as a cytotoxic or a radiosensitizing effect of 3-iodo-L-phenylalanine (IMA) or 4-iodo-L-phenylalanine (IPA) on malignant cells has been described in the art. According to the surprising new findings of the invention a cytotoxic effect of the identified phenylalanine derivatives on all tested malignant cell lines is already detectable for concentrations in a range of 0.1 to 0.3 µmol/ml, which may be roughly translated in a human dose in the range of 7 to 21 mmol/70 kg body weight, corresponding to a dose of 2 to 6 g/kg body weight, assuming even distribution throughout the body. It has been shown, however, that 4-[$^{123}$I] iodo-L-phenylalanine is enriched in certain tumors by a factor of 20 and greater, potentially indicating a clinically effective dose of 100 to 300 mg/70 kg body weight or 1 to 5 mg/kg body weight (8). Moreover, it has been surprisingly found that such phenylalanine derivatives are capable to accumulate specifically in low and high grade gliomas as well as other malignant cells/tissues which can be subsumed under the above provided definition of malignant neoplasia. In contrast, 2-iodo-L-phenylalanine, an example for an ortho-isomer of the 4-(para)iodo-L-phenylalanine (IPA) and the halogenated D-phenylalanine analogues revealed only low uptake and a moderate cytotoxicity in neoplastic cells compared with IPA and IMA. This shows the superior effect of 3-iodo-L-phenylalanine and 4-iodo-L-phenylalanine on malignant cells and tissues compared to other compounds.

The specific accumulation of the 3-iodo-L-phenylalanine and 4-iodo-L-phenylalanine leads to a surprisingly marked retention by the malignant cells or tissue. Thus, the 3-iodo-L-phenylalanine or 4-iodo-L-phenylalanine has a cytostatic effect on such malignant cells or tissue. Moreover, said halogenated-L-phenylalanines such as 4-iodo-L-phenylalanine (IPA) show marked antitumor activities and enhance radiosensitivity in primary tumor cells, including human glioblastoma, prostatic, ovarian and breast cancer, multiple myeloma and malignant melanoma.

With respect to the toxicity of the 3-iodo-L-phenylalanine or 4-iodo-L-phenylalanine it is known in the art for 4-iodo-L-phenylalanine (IPA) that the $LD_{50}$ is >100 mg/kg in rats [9]. The $LD_{10}$ for IPA administered via i.p. injection has been determined in experiments as >27 mg/kg in rats. Moreover, the $LD_{50}$ described for L-phenylalanine administered via i.p. injection is according to the manufacturer 5280 mg/kg in rats. Thus, the toxicity of 3-iodo-L-phenylalanine or 4-iodo-L-phenylalanine is in an acceptable ratio of effectivity vs. toxicity at effective dose levels. Moreover, the transport capacity for IPA in tumor cells did not show saturation up to 200 µmol/L, confirming the relatively high capacity of the transport system also as pathway for tumor therapy. In addition to their cytostatic activity it was found, that 3-iodo-L-phenylalanine and 4-iodo-L-phenylalanine exert a significant intrinsic radiosensitizer effect, which potentiates the cytocidal effect of concomitantly administered therapeutic radiation.

Accordingly, said 3-iodo-L-phenylalanine and 4-iodo-L-phenylalanine represent an attractive new class of compounds for therapeutic pharmaceuticals for the treatment of tumors by which an effective cytotoxic dose can be concentrated selectively on the devastating tumor cells, while sparing the normal tissues. Moreover, the halogenated-L-phenylalanine with iodine in 3- (meta-) or 4-(para-) position are cytostatically active compounds which show favorable tolerability profiles. A therapy using the halogenated-L-phenylalanines 3-iodo-L-phenylalanine or 4-iodo-L-phenylalanine can thereby overcome cellular detoxicfication strategies. Due to the anti-tumor activity the compound is an alternative for maintenance or induction therapy in advanced cancers and for the improvement of the tolerability and efficacy of existing chemotherapy regimens.

In a preferred use of the invention the pharmaceutical composition is to be administered to a subject, wherein 3-iodo-L-phenylalanine or 4-iodo-L-phenylalanine is generally administered in a dose of 0.001 to 100 mg/kg body weight of the subject. More preferably, the 3-iodo-L-phenylalanine or 4-iodo-L-phenylalanine is in a dose of 0.1 to 25 mg/kg body weight of the subject and more preferably, the 3-iodo-L-phenylalanine or 4-iodo-L-phenylalanine is in a dose of 1.0 to 25 mg/kg body weight of the subject.

According to a further preferred use of the invention the halogenated-L-phenylalanine is 4-iodo-L-phenylalanine.

It is preferred that the malignant neoplasia is selected from a group consisting of malignant glioma, multiple myeloma, malignant melanoma, prostatic and breast cancer. More preferably, the glioma is selected from the group consisting of glioblastoma multiforme, anaplastic astrozytoma, astrooligodendroglioma, oligoastrozytoma and ependymoma.

It is further preferred for the use of the invention that the 3-iodo-L-phenylalanine or 4-iodo-L-phenylalanine has on the malignant cells or tissue of the neoplasia a radiosensitizing effect, a cytostatic effect and/or an effect to revert an acquired or constitutive state of cellular resistance to chemotherapy or radiotherapy.

The term "cytostatic effect" describes in the context of the present invention the capacity of a compound to slow down or to arrest the cell proliferation of malignant cells.

The term "radiosensitizing effect" describes in the context of the present invention the capacity of a compound to enhance the therapeutic response to concomitantly administered radiation therapy, wherein the radiation therapy includes external or internal radiation therapy, corresponding to the induction of an increased response to a given radiation dose administered in the presence of the radiosensitizing compound, compared to the response induced by the same radiation dose in the absence of the radiosensitizing compound, or alternatively the selective induction of the sensitivity of neoplastic cells for a radiotherapy, not present in the absence of the compound.

The term "an effect to revert an acquired or constitutive state of cellular resistance to chemotherapy or radiotherapy" describes in the context of the present invention the capacity of a compound to convert or to reconvert the cellular sensitivity for a chemotherapy or a radiotherapy.

Moreover, it is preferred that the pharmaceutical composition further comprises a chemotherapeutic agent, an immunotherapeutic agent, a gene therapeutic agent, a vaccine, an antisense nucleotide therapeutic agent, an siRNA therapeutic agent and/or an endoradiotherapeutic agent.

The administration of a chemotherapeutic agent, an immunotherapeutic agent, a gene therapeutic agent, a vaccine, an antisense nucleotide therapeutic agent, an siRNA therapeutic agent and/or an endoradiotherapeutic agent is understood as a concomitant therapy. Methods and means for such concomitant therapies are well known in the art.

The 3-iodo-L-phenylalanine or 4-iodo-L-phenylalanine and the additional therapeutic agent may be formulated as a single pharmaceutical composition for simultaneous administration of the effective compounds or in separate pharmaceutical compositions for sequential administration. Accordingly, an administration of a composition comprising 3-iodo-L-phenylalanine or 4-iodo-L-phenylalanine prior to the administration of a composition comprising one or more therapeutics selected from the group of a chemotherapeutic, an immunotherapeutic, a gene therapeutic, a vaccine, an antisense nucleotide therapeutic, an siRNA therapeutic and an endoradiotherapeutic agent is envisaged as well as simultaneous or subsequent administration.

An example for a chemotherapeutic agent comprises bioactive agents known to be effective in retarding or arresting the malignant growth or to be effective in the regression or elimination of malignant tissues or cells. Such agents might be e.g. drugs acting as cytostatics. Accordingly, a chemotherapy comprises in line with the medical standards in any systemic or local treatment the administration of cytostatic or cytotoxic agents. Chemotherapeutic agents used in oncology include among others, nitroso urea compounds (ACNU [nimustin], BCNU [carmustin], CCNU [lomustin]), temozolomid, procarbacin, metothrexate, cytarabin, gemcitabine, fluorouracil, cyclophosphamide, mitoxantron, anthracyclins, estramustin, or taxanes. The chemotherapeutic agents are intended to be administered in appropriate dosing regimens according to medical practice. In line with the invention nitroso urea compounds, temozolomide, procarbacin, and methotrexate are preferred chemotherpeutic agents.

Examples for an immunotherapeutic agent comprise but are not limited to compounds such as antibodies, antibody fragments and/or derivatives thereof which specifically detect malignant tissue or cells and/or cellular therapeutics, including those consisting of adoptively transferred autologous, heterologous, xenogenous or endogenous cells, which have the ability to eliminate malignant cells or tissues. The term "antibody fragment or derivative thereof" relates to single chain antibodies, or fragments thereof, synthetic antibodies, antibody fragments, such as Fab, a F(ab2)', Fv or scFv fragments, single domain antibodies etc., or a chemically modified derivative of any of these. Antibodies to be employed in accordance with the invention or their corresponding immunoglobulin chain(s) can be further modified outside the motifs using conventional techniques known in the art, for example, by using amino acid deletion(s), insertion(s), substitution(s), addition(s), and/or recombination(s) and/or any other modification(s) (e.g. posttranslational and chemical modifications, such as glycosylation and phosphorylation) known in the art either alone or in combination. Methods for introducing such modifications in the DNA sequence underlying the amino acid sequence of an immunoglobulin chain are well known to the person skilled in the art; see, e.g., Sambrook et al.; Molecular Cloning: A Laboratory Manual; Cold Spring Harbor Laboratory Press, 2nd edition 1989 and 3rd edition 2001. The specific detection of malignant tissue or cells may be effected via the detection of tumor specific markers by the antibodies, antibody fragments and/or derivatives thereof. A tumor-specific marker is a tumor-associated cell surface antigen which is either found exclusively on tumor cells or is overexpressed on tumor cells as compared to non-malignant cells. Tumor-associated cell surface antigens can be expressed not only on tumor cells but also on cells/tissue which are/is not essential for survival or which can be replenished by stem cells not expressing tumor-associated cell surface antigen. Furthermore, a tumor-associated cell surface antigen can be expressed on malignant cells and non-malignant cells but is better accessible by a therapeutic agent of interest on malignant cells. Examples of over-expressed tumor-associated cell surface antigens are Her2/neu, EGF-Receptor, Her-3 and Her4. An example of a tumor-associated cell surface antigen which is tumor specific is EGFRV-III. An example of a tumor-associated cell surface antigen which is presented on a cell which is non-essential for survival is PSMA. Examples of tumor-associated cell surface antigens which are presented on cells which are replenished are CD19, CD20 and CD33. An example of a tumor-associated cell surface antigen which is better accessible in a malignant state than in a non-malignant state is EpCAM. Moreover, the definition of "immunotherapeutics" may comprise agents such as T-cell co-stimulatory molecules or cytokines, agents activating B-cells, NK-cells or other cells of the immune system as well as drugs inhibiting immune reactions (e.g. corticosteroids).

The term "gene therapeutic agent" defines in the context of the invention means for a therapy comprising the administration of one or more nucleic acid constructs functionally encoding e.g. one or more antigens which are characteristic for malignant cells. Such antigens comprise tumor specific markers. The sequence encoding such antigen is operably linked to a nucleic acid sequence which is a regulatory sequence. Thus, a gene therapy comprises the functional expression of a heterologous gene in a patient according to standard medical protocols using appropriate vector systems known in the art; see e.g. Haberkorn et al., Curr Med Chem. 2005;12(7):779-94. The term "regulatory sequence" refers to DNA sequences which are necessary to effect the expression of coding sequences to which they are ligated. Control sequences in the context of the described gene therapy generally include promoters, terminators and, in some instances, enhancers, transactivators or transcription factors. The term "control sequence" is intended to include, at a minimum, all components the presence of which are necessary for expression, and may also include additional advantageous components. The term "operably linked" refers to an arrangement/configuration wherein the components so described are in a relationship permitting them to function in their intended manner. A control sequence "operably linked" to a coding sequence is ligated in such a way that expression of the coding sequence is achieved under conditions compatible with the control sequences.

The administration of a vaccine aims in the context of the present invention at activating the innate or adaptive immune system of the patient to act against the tumor tissue or the malignant cells. Such therapy comprises e.g. administering one or more antigen preparations containing tumor substances, or cells selected to react against tumor tissue or the malignant cells.

An antisense therapeutic agent is e.g. a nucleotide sequence being complementary to tumor-specific gene sequences, aiming at functionally neutralising tumor gene expression, and consequently inducing tumor cell death.

An siRNA therapeutic agent is e.g. a small interfering RNA capable of sequence-specifically silencing the expression and activity of various tumor-specific target genes by triggering cleavage of specific unique sequences in the mRNA transcript of the target gene and disrupting translation of the target mRNA, consequently inducing tumor cell death.

A concomitant therapy which requires the administration of one or more additional bioactive agents which is/are effective in the treatment of the malignant neoplasia may be accompanied by the administration of one or more additional compounds which minimize potential side effects of said bioactive agent(s) such as drugs acting on the gastrointestinal system, drugs preventing hyperuricemia, and/or drugs acting on the circulatory system, e.g. on the blood pressure, known in the art. Such additional bioactive agents may be formulated in the form of the same or a separate pharmaceutical composition.

The term "endoradiotherapeutic agent" defines in the context of the present invention an agent which comprises at least one type of radioactive isotope. Such agent is to be administered to a subject in the need thereof and is effective in the therapy of the above described malignant neoplasia due to an endogenic irradiation, i.e. an irradiation with the radioactive compound within the body of the subject to be treated by the endoradiotherapy.

In a preferred embodiment the described pharmaceutical composition comprises a combination of 3-iodo-L-phenylalanine or 4-iodo-L-phenylalanine, wherein the iodine is the stable, non-radioactive [$^{127}$I]-iodine isotope and an endoradiotherapeutic agent which is a halogenated-L-phenylalanine, wherein the halogen isotope is selected from the group of alpha-, beta- or Auger-electron emitting isotopes bromine-76, bromine-77, bromine-82, iodine-123, iodine-124, iodine-125, iodine-131 and astatine-211. It is preferred, that the halogen isotope is also conjugated to the L-phenylalanine in 3- (meta-) or 4-(para-) position.

The term "alpha-, beta- or Auger-electron emitting isotope" defines in the context of the present invention radioactive isotopes, characterized by the emission of different particles (rays) formed during radioactive decay or by nuclear transition processes. An alpha emitting isotope is defined as a radioactive nuclide emitting alpha particles, corresponding to a helium nucleus consisting of two protons and two neutrons. A beta emitting isotope is defined as a nuclide emitting fast nuclear electrons (negatrons) formed during radioactive decay. An Auger-electron emitting isotope is defined as a nuclide emitting low energy nuclear electrons, formed by nuclear electron capture or internal transition processes. The maximum path lengths of these particles are in a range from 10 nm to 12 mm.

The physical half life of the recited radionuclides is 16.2 h for bromine-76, 57.04 h for bromine-77, 35.3 h for bromine-82, 13.27 h for iodine-123, 4.17 d for iodine-124, 59.41 d for iodine-125, 8.02 d for iodine-131 or 7.21 h astatine-211. The physical half life of the L-phenylalanine conjugate labelled with these radionuclides corresponds to the half life of the respective radionuclide.

The preferred mixture of 3-iodo-L-phenylalanine or 4-iodo-L-phenylalanine with an endoradiotherapeutic agent is a mixture, wherein the endoradiotherapeutic agent is a halogenated-L-phenylalanine. Preferably, the majority of stable iodine isotopes and some halogen isotopes of the preferred mixture selected from the above identified group of halogen isotopes can be obtained e.g. by a non-isotopic halogen exchange (carrier-added/c.a.). Alternatively, 3-iodo-L-phenylalanine or 4-iodo-L-phenylalanine comprising only the stable, non-radioactive [$^{127}$I]-iodine isotope may be mixed with a preparation of halogenated-L-phenylalanine comprising only or in a majority non-stable, radioactive isotopes. The latter preparation may be obtained e.g. by a no-carrier-added preparation (n.c.a.) which is essentially free from stable isotopes of the element in question. Further alternative mixtures of stable, non-radioactive preparations with non-stable, radioactive preparations are equally preferred.

Generally, it is preferred that the alpha-, beta- or Auger-electron emitting isotope is administered in doses of $10^{-5}$ to $10^{-18}$ g/kg body. More preferably, the alpha-, beta- or Auger-electron emitting isotope is administered in doses of $10^{-7}$ to $10^{-15}$ g /kg body weight and more preferably in doses of $10^{-8}$ to $10^{-10}$ g/kg body weight. It is particularly preferred that such a dose is formulated or contained in 1 to 10, preferably 2 to 5 ml of sterile solution, such as phosphate buffered saline solutions, water for injection, etc.

It is additionally preferred that the irradiation dose of the alpha-, beta- or Auger-electron emitting isotope is in the range of 0.1 to 1000 MBq/kg body weight. More preferably, the irradiation dose of the alpha-, beta- or Auger-electron emitting isotope is in the range of 10 to 400 MBq/kg body weight and more preferably the irradiation dose of the alpha-, beta- or Auger-electron emitting isotope is in the range of 20 to 120 MBq/kg body weight. The administered dose is determined using an appropriate dose meter, calibrated to quantitatively measure alpha, beta or gamma radiation.

It is also preferred that the irradiation dose of the alpha-, beta- or Auger-electron emitting isotope is to be administered as a single dose once or as fractionated doses in 2 to 60 fraction doses or as continuous doses given daily until the disease progresses again, or until death of the patient. As described herein above, the administration of the described pharmaceutical composition results in an interception or a deceleration of the cancer development due to the cytostatic effect of 3-iodo-L-phenylalanine or 4-iodo-L-phenylalanine. Nevertheless, the disease may further progress after the interception or deceleration and the patient may die.

More preferably, the conjugate is to be administered generally fractionized in 2 to 10 fraction doses. It is also preferred that the 3-iodo-L-phenylalanine or 4-iodo-L-phenylalanine is to be administered as a chronic maintenance therapy. It is preferred that the continuous dose is given daily. Dose fractionation is an established procedure in radiation therapy. By fractionating a total administered dose, improved tolerability for healthy non-target tissue, as well as an increased cytotoxic effect to tumor tissue is achieved. Repeated fractionated irradiation allows to therapeutically impact a higher percentage of cells in radiation sensitive stages of the cell cycle, compared to a one time single high dose irradiation. Therapeutic irradiation induces single and double strand breaks of DNA, which is counteracted by nuclear repair mechanisms upregulated following irradiation. It is believed, that cells undergoing DNA repair, are more susceptible to a renewed irradiation than radiation-naive cells.

In a further preferred embodiment the radioactive halogen isotopes are p-[$^{131}$I]iodo-L-phenylalanine (IPA-131), 4-[$^{124}$I]iodo-L-phenylalanine (IPA-124) and/or p-[$^{211}$At]astatine-L-phenylalanine (AtPA-211). Iodine-131 is widely available, has a favourable half life and can be handled by most institutions licensed to apply open radionuclides. Iodine-131 allows for the convenient extracorporal therapy monitoring using a gamma camera owing to a gamma ray component, emitted in a fixed ratio relative to the therapeutic beta particle emission, which is itself not detectable extracorporeally. Another preferred embodiment of the method of the invention makes use of 4-[$^{124}$I]iodo-L-phenylalanine. Iodine-124 has a positron emission component, allowing for PET imaging, in addition to the therapeutic beta-emission. Using quantitative PET imaging, internal dosimetry measurements at an ongoing basis can be conducted for therapy planning and therapy monitoring for a period of up to 15 days following a single injection. Astatine-211 is also preferred, as it emits high energy (6.8 MeV) alpha particles, with a short path length in tissue (65 μm), allowing to administer a highly cytotoxic radiation to targeted tissue, while minimising undesirable radiation effects to non-target tissue.

It is preferred for the use of the invention that the pharmaceutical composition is to be administered to a patient and that this patient is subsequently irradiated percutaneously (percutaneous radiotherapy or external field radiation therapy). Such external field radiation therapy is understood in the context of the invention as a concomitant therapy.

External field radiation therapy is typically administered as an external beam radiation stemming from, among others, radioactive cobalt-60 sources, linear accelerators, proton, neutron, or hadron beam sources. Preferably, the irradiation is started in a period of 0 to 7 days subsequent to the administration of the 3-iodine-L-phenylalanine or 4-iodine-L-phenylalanine. More preferably, the irradiation is started in a period of 0.5 to 24 hours subsequent to the administration of the iodine-L-phenylalanine.

The concomitant radiotherapy may comprise a cumulative external irradiation of a patient in a dose of 1 to 100 Gy. A preferred range of the irradiation dose is 1 to 60 Gy. It is preferred that the external irradiation dose is administered in 1 to 60 fractional doses, more preferably in 5 to 30 fractional doses. Preferably, the fractionized doses are administered over a period of 1 to 26 weeks, more preferably over a period of 6 to 12 weeks. In accordance with the present invention, the term 'fractional dose' is to be understood to mean that the overall activity of the fractional dose adds up or essentially adds up to the cumulative external irradiation otherwise also achievable by administering one single dose.

In an alternative embodiment the invention provides a method for the treatment of malignant neoplasia, the method comprising the steps of administering 3-iodo-L-phenylalanine or 4-iodo-L-phenylalanine to a subject in the need thereof.

It is preferred that the effective compound 3-iodo-L-phenylalanine or 4-iodo-L-phenylalanine is formulated in form of a pharmaceutical composition. The term "pharmaceutical composition" has been defined herein above. The route of administration of the effective compound depends inter alia on its formulation. Different routes for differentially formulated compositions have been described herein above. It is particularly preferred for the method of the invention that the 3-iodo-L-phenylalanine or 4-iodo-L-phenylalanine is administered intravenously or orally.

It is further preferred that the 3-iodo-L-phenylalanine or 4-iodo-L-phenylalanine is administered to the subject in a doses of 0.001 to 100 mg/kg body weight of the subject. More preferably, the 3-iodo-L-phenylalanine or 4-iodo-L-phenylalanine is administered in a dose of 0.1 to 25 mg/kg body weight of the subject and more preferably, the 3-iodo-L-phenylalanine or 4-iodo-L-phenylalanine is in a dose of 1.0 to 25 mg/kg body weight of the subject.

Also preferred for the method for the treatment of malignant neoplasia of the invention is the administration of 3-iodo-L-phenylalanine or 4-iodo-L-phenylalanine to a subject in the need thereof, wherein the halogenated-L-phenylalanine is 4-iodo-L-phenylalanine.

As defined herein above, it is preferred that the malignant neoplasia is selected from a group consisting of malignant glioma, multiple myeloma, malignant melanoma, prostatic and breast cancer. More preferably, the glioma is selected from the group consisting of glioblastoma, astrozytoma, oligoastrozytoma and ependymoma.

It is also preferred for the method of the invention that the 3-iodo-L-phenylalanine or 4-iodo-L-phenylalanine has on the malignant cells or tissue of the neoplasia a radiosensitizing effect, a cytostatic effect and/or an effect to revert an acquired or constitutive state of cellular resistance to chemotherapy or radiotherapy.

A preferred administration scheme for the administration of the 3-iodo-L-phenylalanine or 4-iodo-L-phenylalanine is either the administration of a single dose once or a sequential administration of 3-iodo-L-phenylalanine or 4-iodo-L-phenylalanine as fractionated doses in 2 to 60 fraction doses or a continuous dose given until the disease progresses again or until death of the patient/subject. Thus, it is also preferred that the 3-iodo-L-phenylalanine or 4-iodo-L-phenylalanine is administered as a chronic maintenance therapy. It is preferred that the continuous dose is given daily.

In an also preferred embodiment of the method of the invention for the treatment of malignant neoplasia it is envisaged that the method further comprises the step of treating the subject by a concomitant therapy. Said concomitant therapy may be selected from the group consisting of a surgical therapy, a chemotherapy, an endo- or exoradiotherapy, an immunotherapy, a gene therapy, a vaccine therapy, an antisense nucleotide therapy, an siRNA therapy, an intracavitary therapy, or a device-based treatment.

Definitions for a chemotherapy, an endoradiotherapy or external field radiation therapy (in the following: exoradiotherapy), an immunotherapy, a gene therapy, a vaccine therapy, an antisense nucleotide therapy and an siRNA therapy are provided herein above.

Methods and means for such concomitant therapies are well known in the art. An example for a surgical therapy may comprise a resection of a solid tumour or of malignant tissue.

A further concomitant therapy in line with the invention comprises the surgical implantation of a radioactive device such as a radioactive seed. Such a seed may be implanted locally to the tumor site. The technique of implanting radioactive devices is known in the art and described herein above in the discussion of the state of the art. The dose regimen for the administration of the 3-iodo-L-phenylalanine or 4-iodo-L-phenylalanine is preferably in timely accordance with the optional concomitant therapy (e.g. a concomitant external field radiation therapy or a concomitant endoradiotherapy). It is also preferred, that 3-iodo-L-phenylalanine or 4-iodo-L-phenylalanine is administered as a chronic maintenance therapy given in combination with other agents to a tumor patient until the disease progresses again or until the death of the patient.

As described above in the context of the use of the invention, a method of the invention is preferred, wherein the concomitant therapy is an exoradiotherapy comprising the step of irradiating the subject percutaneously subsequently to the administration of the 3-iodo-L-phenylalanine or 4-iodo-L-phenylalanine. More preferably, the step of irradiating is effected 0 to 7 days subsequent to the administration of the 3-iodo-L-phenylalanine or 4-iodo-L-phenylalanine. Even more preferably, the irradiation is started in a period of 0.5 to 24 hours subsequent to the administration of the 3-iodo-L-phenylalanine or 4-iodo-L-phenylalanine.

The above described concomitant radiotherapy may comprise a cumulative external irradiation of a patient in a dose of 1 to 100 Gy. A preferred range of the irradiation dose is 1 to 60 Gy. It is preferred that the external irradiation dose is administered in 1 to 60 fractional doses, more preferably in 5 to 30 fractional doses. Preferably, the fractionized doses are administered over a period of 1 to 26 weeks, more preferably over a period of 6 to 12 weeks. In accordance with the present invention, the term 'fractional dose' is to be understood to mean that the overall activity of the fractional dose adds up or essentially adds up to the cumulative external irradiation otherwise also achievable by administering one single dose.

It is also preferred that the above described concomitant therapy comprises the administration of a chemotherapeutic agent, an immunotherapeutic agent, a gene therapeutic agent, an antisense nucleotide therapeutic agent, an siRNA therapeutic agent, a vaccine and/or an endoradiotherapeutic agent or the implantation of a radioactive device. More preferably, the administration of a chemotherapeutic agent, an immunotherapeutic agent, a gene therapeutic agent, an antisense nucleotide therapeutic agent, an siRNA therapeutic agent, a vaccine and/or an endoradiotherapeutic agent is effected prior to, simultaneously and/or subsequently to the administration of the 3-iodo-L-phenylalanine or 4-iodo-L-phenylalanine.

It is preferred that the subject to be treated by the method of the invention is a human subject.

In a further alternative embodiment the invention relates to a pharmaceutical composition comprising 3-iodo-L-phenylalanine or 4-iodo-L-phenylalanine, wherein the iodine is the stable, non-radioactive [$^{127}$I]-iodine isotope.

Pharmaceutical compositions in the context of the present invention have been described in detail herein above. It is preferred that the pharmaceutical composition of the invention further comprises suitable formulations of carrier, stabilizers and/or excipients. Examples for corresponding carrier, stabilizers and/or excipients are known by the person skilled in the art and have been characterized herein above.

The figures show:

FIG. 1:

Cellular uptake kinetics of IPA (IPA-123) in human glioma cell lines in vitro

FIG. 2:

Cellular uptake kinetics of IPA (IPA-123) in human malignant melanoma cell lines in vitro

FIG. 3:

Cellular uptake kinetics of IPA (IPA-123) in human prostate cancer cell lines in vitro

FIG. 4:

In vitro evaluation of IPA (ACD-101) in primary human Tx3868 glioblastoma cells 4a ( top left): Dose dependent cytostatic effect of IPA on human Tx3868 glioblastoma cells; 4b (top right): Effect of different doses of external radiation on human Tx3868 glioblastoma cells alone; 4c (bottom left): Dose dependent radiosensitiser effect of IPA administered concomitantly with 5 Gy external radiation on human Tx3868 glioblastoma cells; 4d (bottom right): Dose dependent radiosensitiser effect of IPA administered concomitantly with 10 Gy external radiation on human Tx3868 glioblastoma cells

FIG. 5:

In vitro evaluation of IPA(ACD-101) and external radiation in human A1207 glioblastoma cells 5a (top left): Effect of different doses of external radiation on human A1207 glioblastoma cells alone; 5b (top right): Cytostatic and radiosensitiser effect of 0.1 mg/ml IPA administered concomitantly with 0-15 Gy external radiation on human A1207 glioblastoma cells; 5c (bottom left): Cytostatic and radiosensitiser effect of 0.2 mg/ml IPA administered concomitantly with 0-15 Gy external radiation on human A1207 glioblastoma cells; 5d (bottom right): Cytostatic and radiosensitiser effect of 0.3 mg/ml IPA administered concomitantly with 0-15 Gy external radiation on human A1207 glioblastoma cells

FIG. 6:

In vitro evaluation of IPA(ACD-101) in human M059K glioblastoma cells 6a (top left): Effect of different doses of external radiation on human M059K glioblastoma cells alone; 6b (top right): Cytostatic and radiosensitiser effect of 0.1 mg/ml IPA administered concomitantly with 0-15 Gy external radiation on human M059K glioblastoma cells; 6c (bottom left): Cytostatic and radiosensitiser effect of 0.2 mg/ml IPA administered concomitantly with 0-15 Gy external radiation on human M059K glioblastoma cells; 6d (bottom right): Cytostatic and radiosensitiser effect of 0.3 mg/ml IPA administered concomitantly with 0-15 Gy external radiation on human M059K glioblastoma cells

Figure 7:
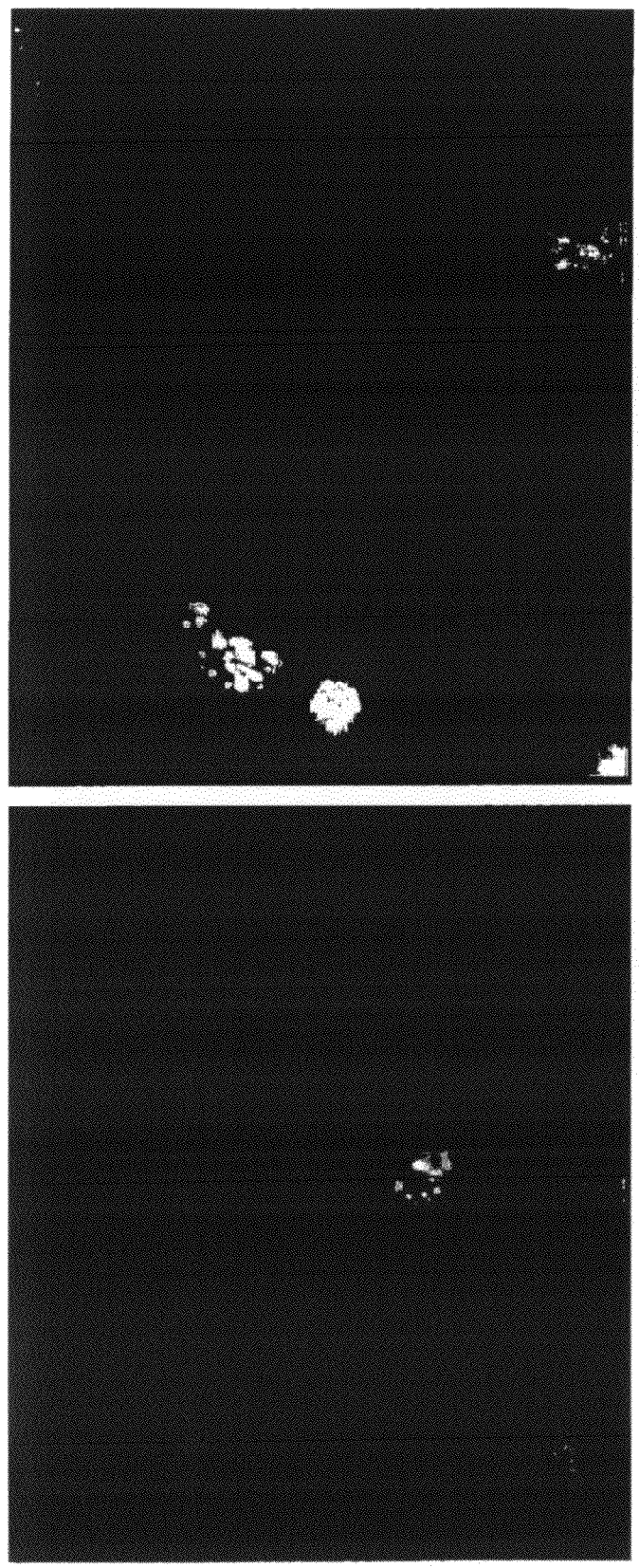

FIG. 7:

Dose dependent induction of primary necrosis and apoptosis by IPA+external irradiation (10 Gy) in human T3868 glioblastoma cells Dose dependent radiosensitiser effect of IPA administered concomitantly with 10 Gy external radiation on human Tx3868 glioblastoma cells: induction of necrosis (iodbenzimid staining) by 0.1 µmol/ml (FIG. 7a (left)), increased induction of necrosis and additional induction of apoptosis (propidium iodide staining) by 0.3 µmol/ml (FIG. 7b (right))

FIG. 8:

Kaplan-Meyer estimates of survival, in RNU rats, which received an orthotopic (intracerebal) implantation of $0.5*10^6$ A1207 cells, a human glioblastoma cell line. Survival of control animals (green), and rats receiving 1 mg/kg daily i.p. injection of IPA The invention will now be described by reference to the following examples which are merely illustrative and are not to be construed as a limitation of scope of the present invention.

EXAMPLE 1

3-Iodo-L-phenylalanine (3-IPA), 4-[$^{123}$I]iodo-L-phenylalanine and 4-iodo-L-phenylalanine (IPA) used in the examples were purchased commercially or prior synthesized as described previously in the literature. Unless stated otherwise, all other chemicals and solvent were of analytical grade.

EXAMPLE 2

Cell Lines and Cell Cultures

Five human glioma cell lines, one rat glioma cell line, two human prostate cancer cell lines, as well as one human breast cancer cell line, and a melanoma cell line were investigated. The human glioma cell lines Tx 3868 and T 5135 (from primary human glioblastoma multiforme), and the rat C6 glioma cells were provided by the Institute of Human Genetics, University of the Saarland (Homburg, Germany). The human high-grade glioma cells, designated as A1207, M059K and U373MG, the human prostate cancer cells PC3 and DU425, the pancreatic carcinoma cell line PanC1, the human breast cancer cell line MCF-07 (American Type Culture Collection, Rockville, Md.), and the pancreatic carcinoma cell line PaCa44 (established by Dr Bulow, Mainz, Germany) as well as the melanoma cell lines SK-MEL25 and A101D were purchased commercially or provided by the oncological research laboratory of the University Medical Center of Saarland (Homburg, Germany). Cells were cultivated in RPMI-1640 medium or in Dulbecco's modified Eagle medium (sodium pyruvate-free, supplemented with L-glucose and pyridoxine), respectively, supplemented with 10% (v/v) heat-inactivated foetal calf serum (FCS), penicillin (50 U/ml), streptomycin (50 µg/ml), and insulin (50 µg/ml; PromoCell, Heidelberg, Germany). All cell lines were maintained in appropriate flasks in a humidified incubator (5% $CO_2$) at 37° C. Before the experiment, subconfluent cell cultures were trypsinized with a solution of 0.05% trypsin containing 0.02% EDTA but without $Ca^{2+}$ and $Mg^{2+}$, and resuspended in fresh medium to various cell concentrations after counting by vital staining on a hemocytometer, depending upon the study. Cells were free of mycoplasms. Viability of the cells was >95%.

EXAMPLE 3

Example of Internalisation Experiments

Uptake experiments were undertaken to evaluate the affinity of the proposed L-phenylalanine derivatives for the proposed human tumors, and to assess their therapeutic activity in vitro.

All experiments were performed fourfold, simultaneously with 250000, 500000 and $10^6$ freshly prepared human tumor cells, including human malignant glioma cells, pancreatic prostatic and breast cancer cells. Before experiments, subconfluent cells were trypsinized as described above. The suspension was mixed thoroughly, transferred to a 50-ml centrifuge tube (Falcon®, Becton Dickinson, USA). Cells were centrifuged for 5 min at 200×g; the resulting supernatant was removed and the pellet resuspended in serum-free Dulbecco's Mod Eagle medium and then transferred to Eppendorf tubes at concentrations of $10^6$ cells/ml for the uptake investigations.

Before incubation with the corresponding radiolabeled phenylalanine, the tumor cells were preincubated for 5 min in 500 µL medium at 37° C. in 1.5-ml Eppendorf centrifuge tubes. Aliquots of 30-50 µL ($10^6-1.5 \times 10^6$ cpm) freshly prepared radiopharmaceutical were added and cells incubated at 37° C./5% $CO_2$ for 1, 2, 5, 15, 30, 60, 90 and 120 min while shaking. Uptake was stopped with 500 µL ice-cold PBS (pH 7.4) and an additional 3-min in an ice bath, the cells were centrifuged for 2 min at 300×g, the supernatant removed and the pellet washed three time with ice-cold PBS. Cell pellets were counted for radioactivity together with 3 aliquots of standards on a Berthold LB951 counter. The percentage of binding of the radiopharmaceutical was calculated by the formula: (cpm cell pellet/mean cpm radioactive standards)×100. The results were expressed either as percent of the applied dose per $10^6$ cells or as cpm/1000 cells for better comparison.

EXAMPLE 4

Evaluation of the cell survival rate after treatment with 3/4-iodo-L-phenylalanine. After development of a confluent lawn of cells, the cultures were exposed to 0.1-5 µmol/ml of the corresponding pharmaceutical for up to 48 hours at 37° C./5% $CO_2$. In a parallel experiment, cells were irradiated using a 6-MeV linear accelerator with doses from 2 to 15 Gy or treated with IPA-131 for comparison of cell survival rate. In order to be able to observe the morphology of the glioma cells, the cells were grown on standard glass slides or in standard culture dishes. Then the medium was removed and the cells were fixed either in 70% ethanol for at least 30 min on ice for flow-cytometric analyses after staining or in 4% neutral buffered formalin for immunohistopathological analyse.

EXAMPLE 5

Tumor Models

An in vivo experiment was carried out in an intracranial human glioma model in RNU rats to assess the therapeutic effectiveness of 4-Iodo-L-phenylalanine (IPA) in glioma.

Primary human A1207 and T3868 glioblastoma cells (0.5× $10^6$ cells) were stereotaxically implanted into the right frontal region of RNU rats (2 mm posterior and 2 mm lateral to the intersection of the sagittal and bregma sutures to a depth of 5 mm) while under chloralhydrate anesthesia. The craniectomy was resealed with bone wax and the scalp closed.

IPA (1 and 5 mg/kg b.w.) was administrated i.p. in rats bearing human glioblastoma xenografts (n=9 in each group), starting at day 1 after stereotaxic implantation.

IPA was administrated daily in the first week after implantation and weekly afterwards. Another six RNU rats were treated with saline and served as control.

Then the following parameters were compared: median survival time, tumor size and histology after biopsy.

EXAMPLE 6

Morphological and Histological Examinations

Human tumor cells grown on standard glass slides were fixed in 4% neutral buffered formalin and stained with the Giemsa method. The cell number was calculated in 10 consecutive high power fields (×40).

At autopsy of the rats, besides the brains, other organs were harvested including the heart, lung, liver, spleen, kidney, skin, and colon. The brains were cut in coronal slices of about 2-3 mm thickness. All tissues from the animals were fixed in 4% neutral buffered formalin and embedded in paraffin wax. Sections were stained with hematoxylin-eosin and Verhoeff-van Gieson and examined histopathologically.

EXAMPLE 7

Statistical Analysis

The statistical significance of differences among experimental groups was determined by Student's t-test. A p-value less than 0.05 was considered significant.

EXAMPLE 8

Results and Discussion

In Vitro Studies

Figure 2:
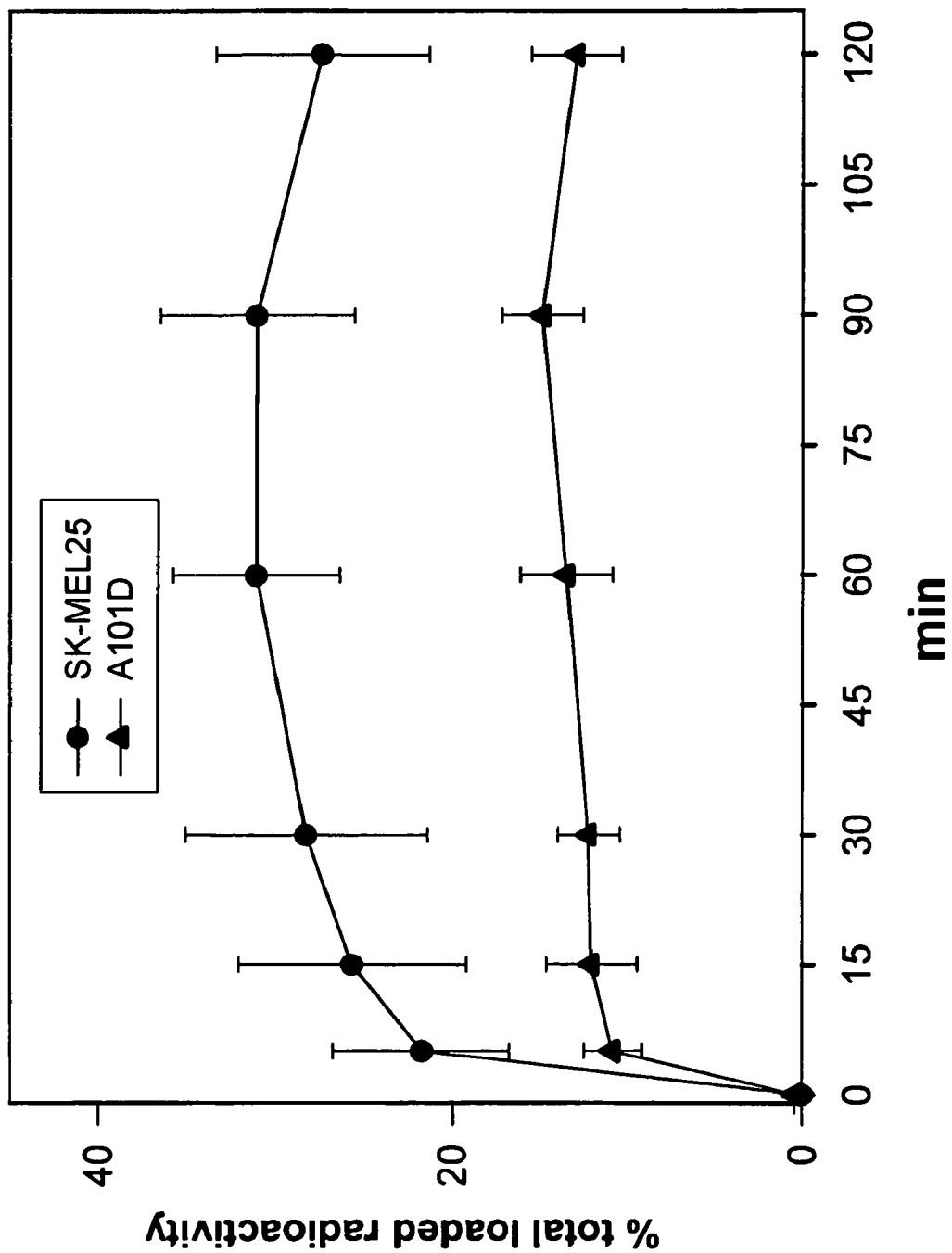
Figure 3:
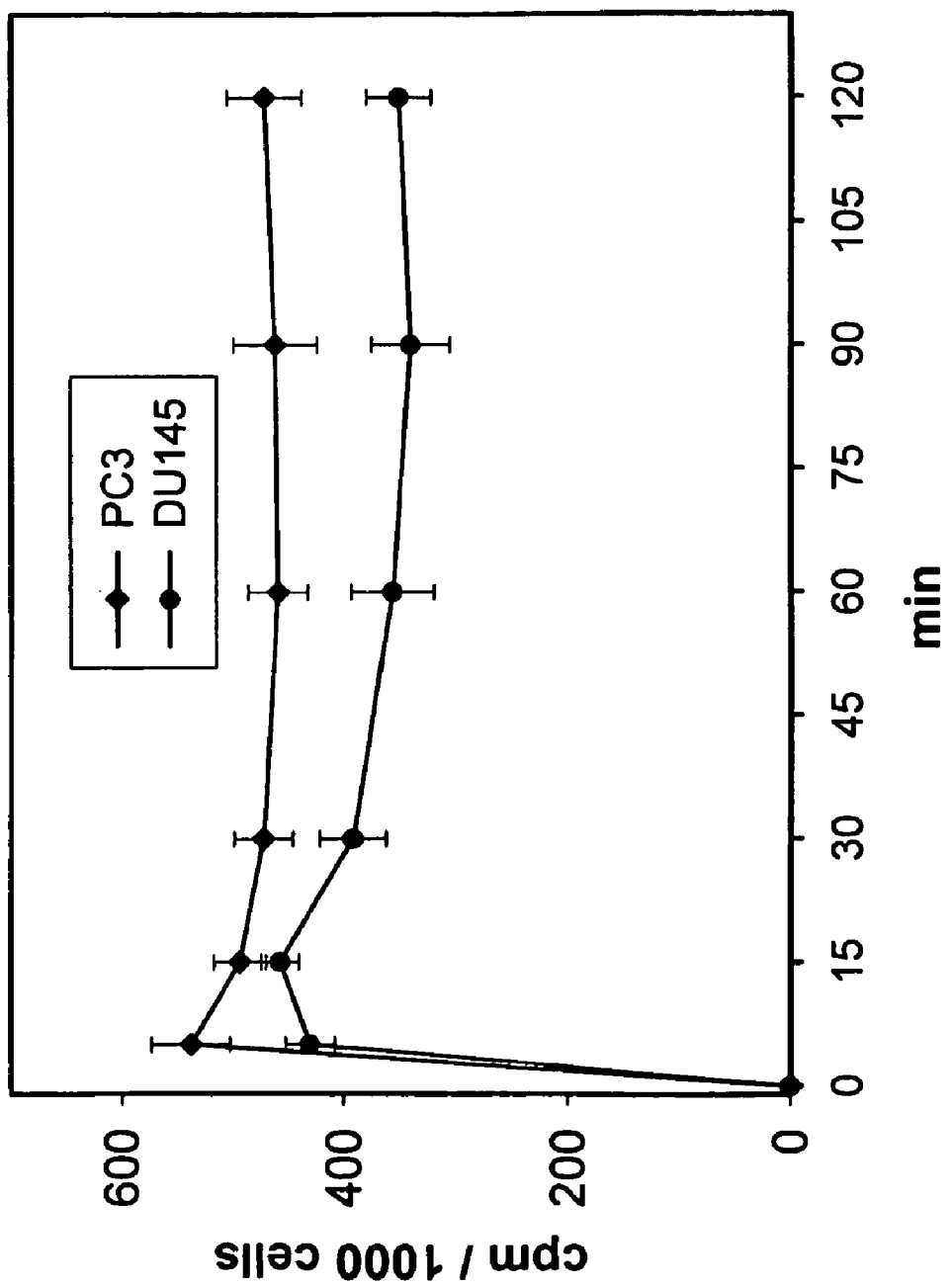

FIGS. 1-3 show examples of uptake kinetics of an IPA in human tumor cells. The radiolabeled derivative 4-[$^{123}$I]iodo-L-phenylalanine was used to facilitate quantification, using a gamma counter. As shown, IPA exhibit high uptake in human tumor cells with a continuous increase over the investigation time. This result provides evidence of the high affinity of the proposed radiopharmaceuticals for human tumors, including the human malignant gliomas, pancreatic carcinomas, prostate and breast cancer.

Figure 4:
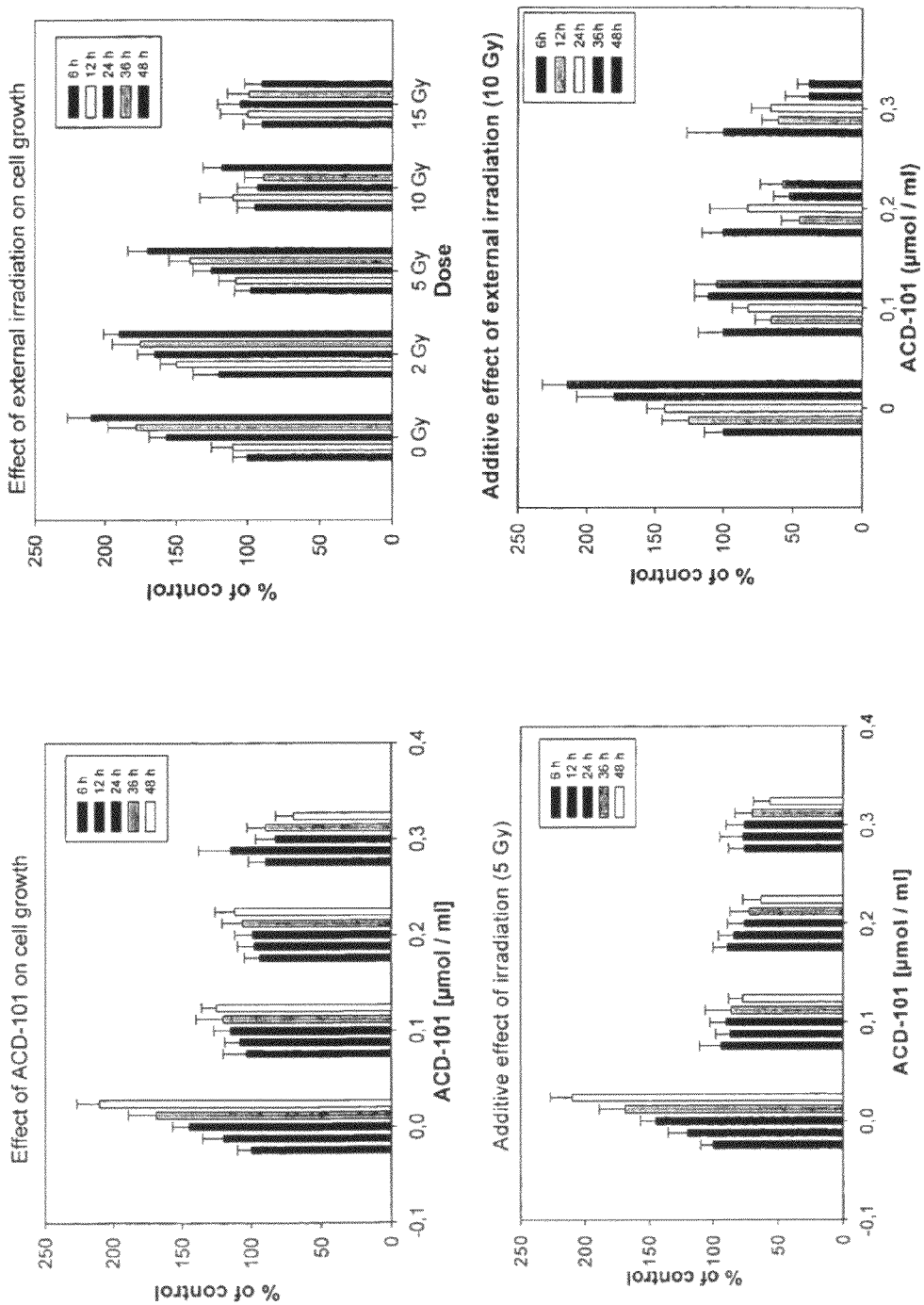
Figure 5:
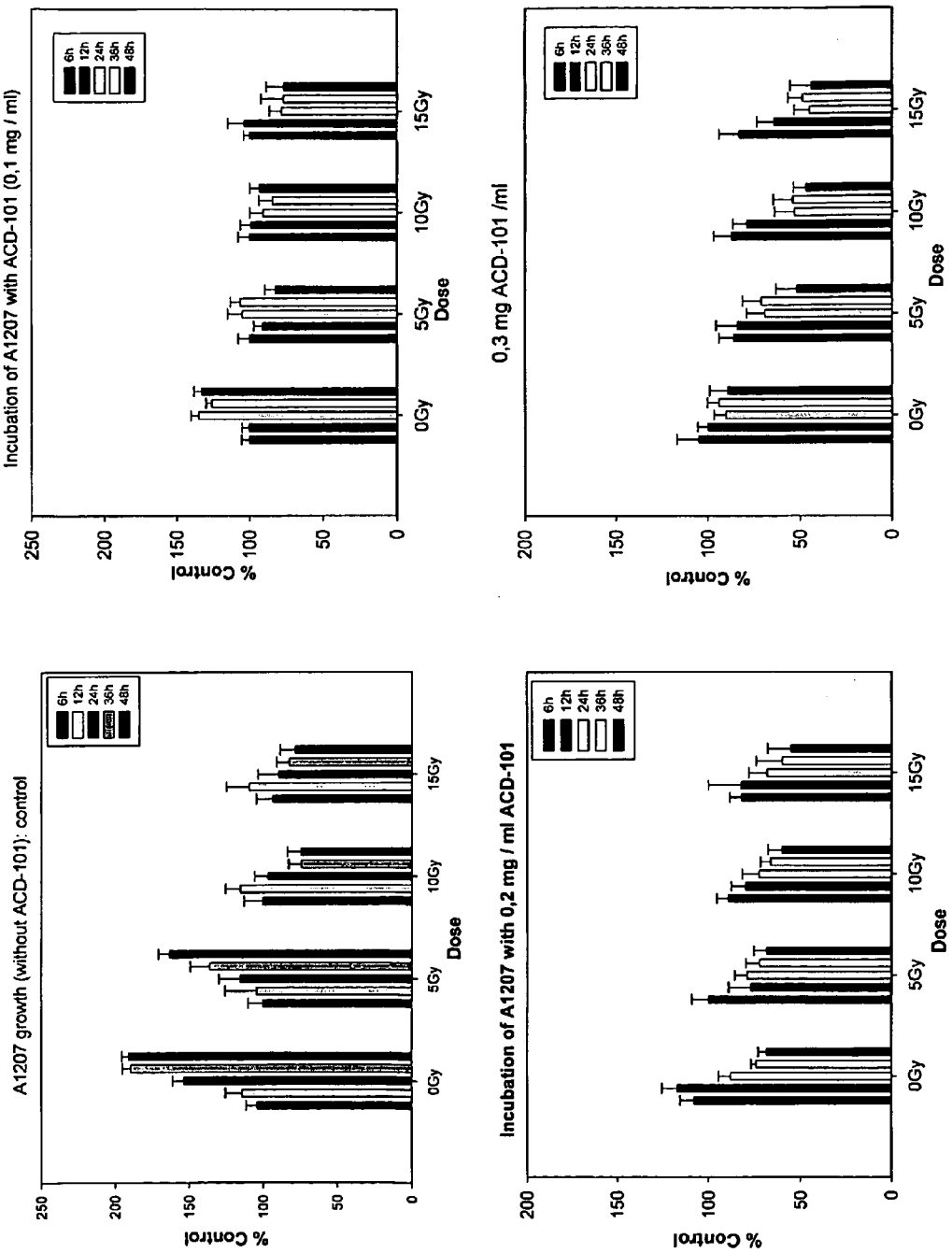
Figure 6:
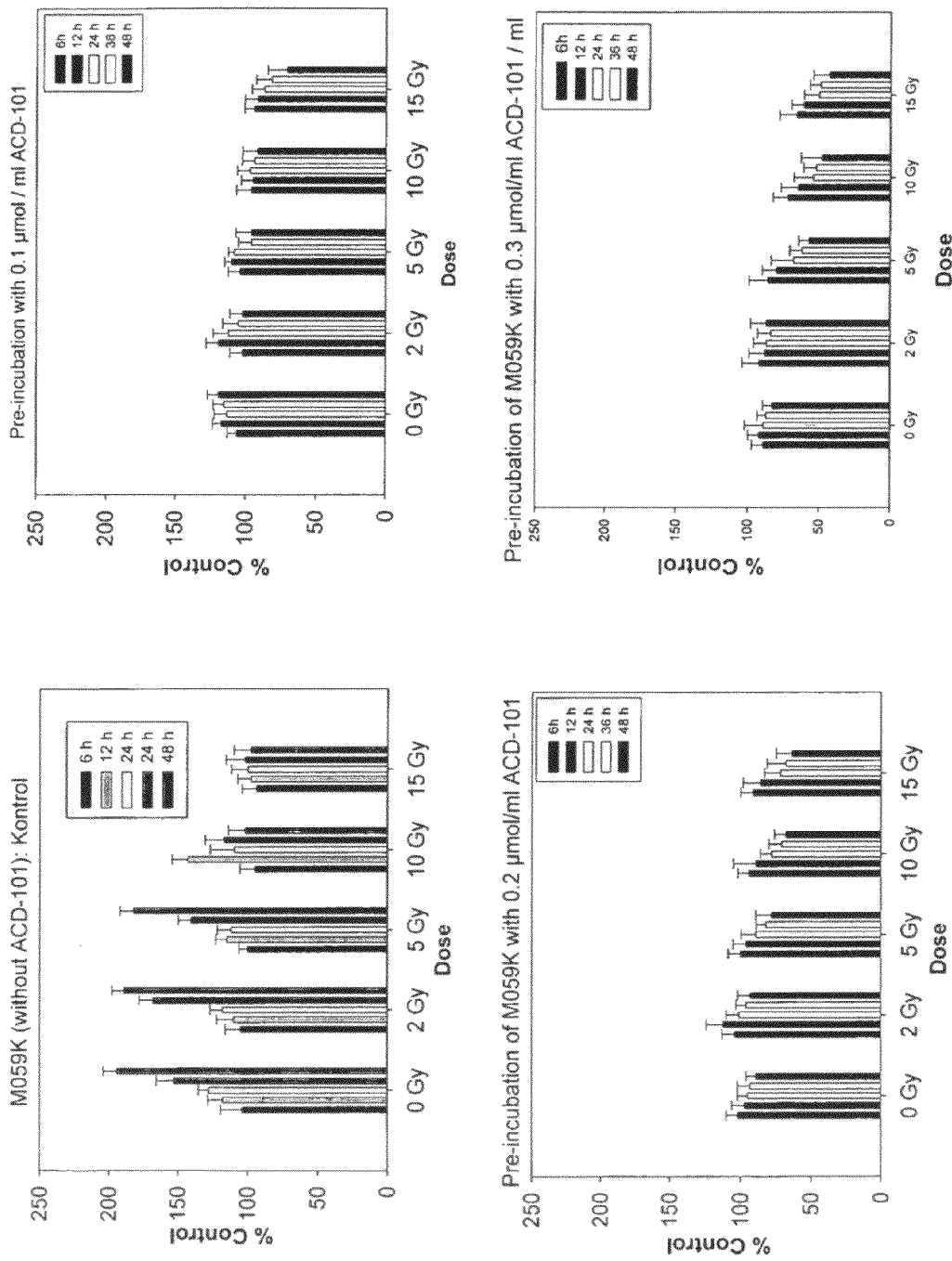

The cytostatic effect and radiosensitizing effect of IPA in glioma cells are demonstrated in FIGS. 4-6. As shown, the cytostatic effect of IPA on primary human glioblastoma cells is concentration dependent and more pronounced as compared to external irradiation up to 15 Gy (FIG. 4). Combining IPA with external irradiation led to a dramatic reduction of cell survival rate. Flow-cytometric analyses of stained cells show dose dependent induction of primary necrosis and apoptosis, which was more significant than that caused by external irradiation, even with 15 Gy, and more pronounced with increasing IPA-concentration. This result attests the high radiosensitizing effect of IPA on glioblastoma cells (FIG. 6). The surviving cells contained only sparse cytoplasm, the nuclei were shrunken and contained clumped chromatin. Cytologically, the mode of cell death was apoptosis as the remaining tumour cells contained only sparsely cytoplasm and apoptotic bodies, in other cells the nuclei were shrunken and contained condensed chromatin.

In Vivo Studies

Five out of six untreated rats with A1207 glioblastoma died 12 to 22 days after implantation while four out of six control rats with T3868 died within 28 days. Histological examination of thin brain sections after biopsy confirmed tumors with typical glioblastoma characteristics. In comparison, six out of nine and seven out of nine rats were still alive at day 28 by treatment with IPA (1 and 5 mg/kg), respectively.

Figure 8:
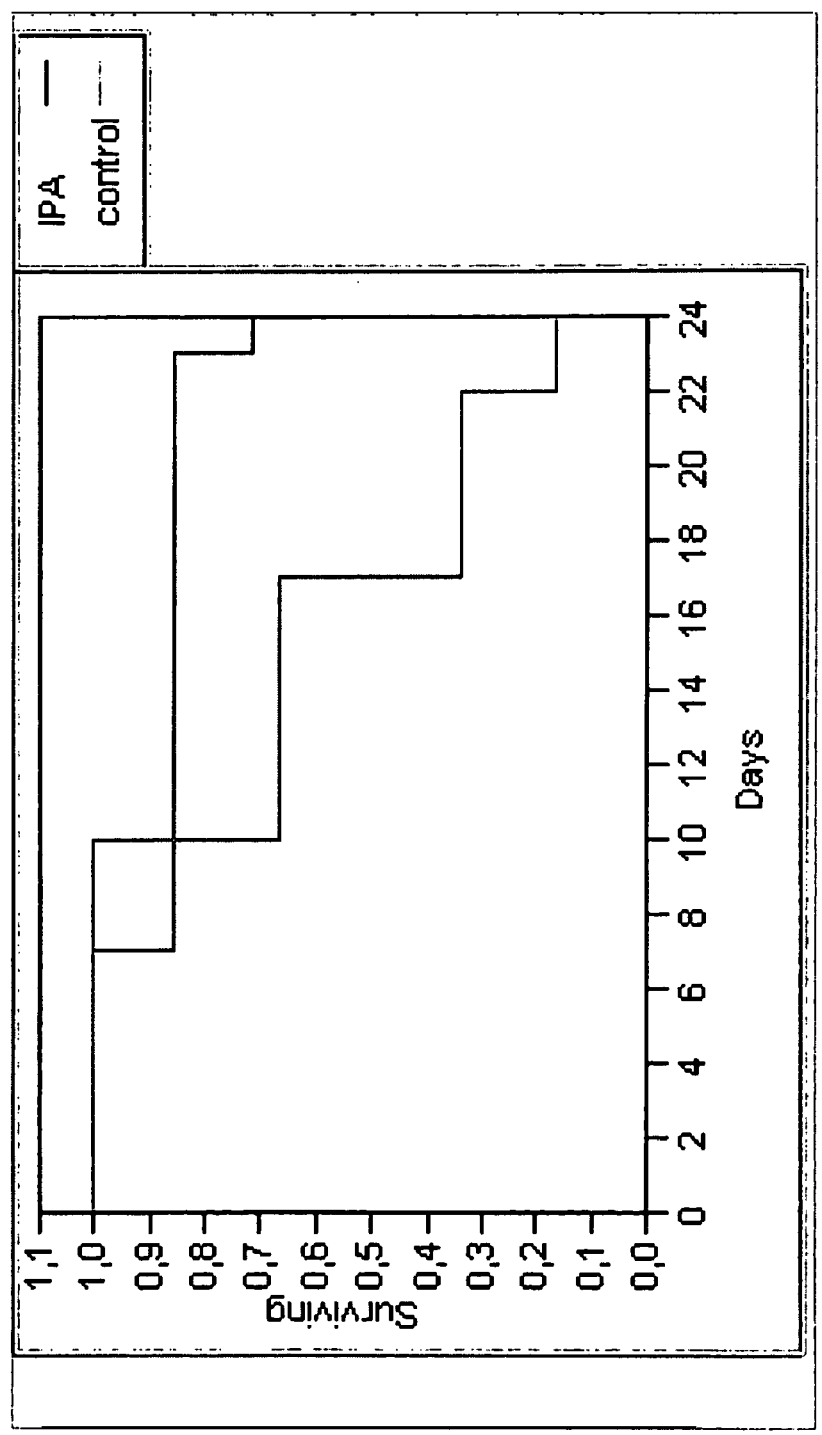

FIG. 8 shows an example of survival of untreated and IPA-treated rats with human A1207 glioblastomas according to the Kaplan-Meier method, attesting the effectiveness of IPA in treating gliomas.

These results suggest a high therapeutic potential of 4-iodo-L-phenylalanine for human tumors, especially for malignant gliomas.

The results demonstrate that 3-iodo-L-phenylalanine and 4-iodo-L-phenylalanine represent a new class of therapeutic agents for tumour therapy in some tumor entities.

REFERENCES

1. Hortobagy G, Cancer Control 4; suppl., 1997
2. O'Day S et al., Cancer Control 9: 31-38, 2002
3. Nieto Y et al. Biology of blood and marrow transplantation 11: 297-306, 2005
4. Carlson K et al. Bone marrow transplantation 35: 985-90, 2005
5. Gruenhagen D et al. Annals of surgery 240: 939-47, 2004
6. Jager P L, Vaalburg W, Pruim J, de Vries E G, Langen K J, Piers D A. Radiolabeled amino acids: basic aspects and clinical applications in oncology. *J Nucl Med* 2001; 42: 432-445.
7. Laverman P, Boerman O C, Corstens F H, Oyen W J. Fluorinated amino acids for tumour imaging with positron emission tomography. *Eur J Nucl Med Mol Imaging* 2002; 29: 681-690.
8. Hellwig D, Ketter R, Romeike B F, Sell N, Schaefer A, Moringlane J R, Kirsch C M, Samnick S: Validation of brain tumour imaging with p-[$^{123}$I]iodo-L-phenylalanine and SPECT. Eur J Nucl Med Mol Imaging 32: 1041-1049, 2005.
9. S. Samnick, D. Hellwig, B. F. Romeike, J.-R. Moringlane, W. Feiden and C.-M. Kirsch. Initial Evaluation on the feasibility of single photon emission tomography with L-p-[$^{123}$I]Iodophenylalanine for routinely brain tumor imaging. Nucl Med Commun 23:121-130, 2002.
10. Fukushima K, Toyoshima S. Antitumor activity of amino acid derivatives in the primary screening. Gann. 66(1):29-36, 1975.
11. Otani T T, Briley M R. Structure-activity relationships among substituted N-benzoyl derivatives of phenylalanine and its analogues in a microbial antitumor prescreen III: derivatives of p-fluoro-DL-phenylalanine. J Pharm Sci. 74(1):40-43, 1985.
12. Loeffler L J, Sajadi Z, Hall I H. Antineoplastic agents. 2. Structure-activity studies on N-protected vinyl, 1,2-dibromoethyl, and cyanomethyl esters of several amino acids. J Med Chem 20: 1584-1588, 1977.
13. Otani T T, Briley M R. m- And p-halobenzoyl derivatives of p-halo-DL-phenylalanine as inhibitors in a microbial antitumor prescreen. Res Commun Chem Pathol Pharmacol. 40(2): 325-8, 1983
14. Otani T T, Briley M R. The study of structure-activity relationships among substituted N-benzoyl derivatives of phenylalanine and its analogs in a microbial antitumor prescreen: II. Derivatives of m-fluoro-DL-phenylalanine. Res Commun Chem Pathol Pharmacol 40: 321-324, 1983.
15. Kelly C J, Johnson T C.: Effects of p-chlorophenylalanine and alpha-methylphenylalanine on amino acid uptake and protein synthesis in mouse neuroblastoma cells. Biochem J. 1978 15;174(3):931-8.
16. Prohaska J R, Wells W W, Luecke R W.: Effect of phenylalanine and p-chlorophenylalanine administration on the development of rat brain 2',3'-cyclic nucleotide 3'-phosphohydrolase. Proc Soc Exp Biol Med. 1974;147(2):566-71.

17. Warters R L, Hofer K G, Harris C R, Smith J M. Radionuclid toxicity in cultured mammalian cells: Elucidation of the primary site of radiation damage. Curr Top Radiat Res Quar 12: 389-407, 1977.
18. Zalutsky M R, Bigner D D: Radioimmunotherapy with alpha-particle emitting radioimmunoconjugates. Acta Oncol 35: 373-379, 1996.
19. Hofer K G, Keough G, Smith J M. Biological toxicity of Auger emitters: molecular fragmentation versus electron irradiation. Curr Top Radiat Res Quar 12: 335-354, 1977.
20. Behr T M, Wormann B, Gramatzki M, Riggert J, Gratz S, Behe M, Griesinger F, Sharkey R M, Kolb H J, Hiddemann W, Goldenberg D M, Becker W: Low- versus high-dose radioimmunotherapy with humanized anti-CD22 or chimeric anti-CD20 antibodies in a broad spectrum of B cell-associated malignancies. Clin Cancer Res 5: 3304-3314, 1999.

The invention claimed is:

1. A method for the treatment of a malignant neoplasia, the method comprising the step of administering 3-iodo-L-phenylalanine or 4-iodo-L-phenylalanine to a subject in the need thereof, wherein the iodine is the stable, non-radioactive [$^{127}$I]-iodine isotope, wherein the malignant neoplasia is selected from the group consisting of malignant glioma, multiple myeloma, malignant melanoma and breast cancer.

2. The method according to claim 1, wherein the 3-iodo-L-phenylalanine or 4-iodo- L-phenylalanine is administered to the subject in a doses of 0.001 to 100 mg/kg body weight of the subject.

3. The method according to claim 1, wherein 4-iodo-L-phenylalanine is administered to the subject.

4. The method according to claim 1, wherein the glioma is selected from the group consisting of glioblastoma, astrozytoma, oligoastrozytoma and ependymoma.

5. The method according to claim 1, wherein the 3-iodo-L-phenylalanine or 4-iodo- L-phenylalanine has on the malignant cells or tissue of the neoplasia a radiosensitizing effect, a cytostatic effect and/or an effect to revert an acquired or constitutive state of cellular resistance to chemotherapy or radiotherapy.

6. The method according to claim 1, wherein the 3-iodo-L-phenylalanine or 4-iodo- L-phenylalanine is administered intravenously or orally.

7. The method according to claim 1, wherein the 3-iodo-L-phenylalanine or 4-iodo- L-phenylalanine is administered as a single dose once, as fractionated doses in 2 to 60 fraction doses, or as continuous doses given daily until the disease progresses again, or until death of the subject.

8. The method according to claim 1, further comprising the step of treating the subject by a concomitant therapy selected from the group consisting of a surgical therapy, a chemotherapy, an endo- or exoradiotherapy, an immunotherapy, a gene therapy, an antisense nucleotide therapy, an siRNA therapy, an intracavitary therapy, or a device- based treatment.

9. The method according to claim 8, wherein the concomitant therapy is an exoradiotherapy comprising the step of irradiating the subject percutaneously subsequently to the administration of the 3-iodo-L-phenylalanine or 4-iodo-L-phenylalanine.

10. The method according to claim 9, wherein the step of irradiating is effected 0 to 7 days subsequent to the administration of the 3-iodo-L-phenylalanine or 4- iodo-L-phenylalanine.

11. The method according to claim 10, wherein the step of irradiating is effected in a cumulative external irradiation of a patient in a dose of 1 to 100 Gy.

12. The method according to claim 8, wherein the concomitant therapy comprises the administration of a chemo therapeutic, an immunotherapeutic, a gene therapeutic, an antisense nucleotide therapeutic, an siRNA therapeutic, a vaccine and/or an endoradiotherapeutic agent or the implantation of a radioactive device.

13. The method according to claim 12, wherein the administration of a chemo therapeutic, an immunotherapeutic, a gene therapeutic, an antisense nucleotide therapeutic, an siRNA therapeutic, a vaccine and/or an endoradiotherapeutic agent is effected prior to, simultaneously and/or subsequently to the administration of the 3-iodo-L-phenylalanine or 4-iodo-L- phenylalanine.

14. The method of claim 8, wherein the endroradiotherapy comprises a halogenated-L-phenylalanine and further wherein the halogen isotope is selected from the group consisting of alpha-, beta- or Auguer-electron emitting isotopes bromine-76, bromine-77, bromine-82, iodine-123, iodine-124, iodine-125, iodine-131 and astatine-211.

15. The method of claim 14, wherein the halogen isotope is conjugated to the L-phenylalanine in 3-(meta) or 4-(para) position.

16. The method according to claim 1, wherein the subject is a human subject.

* * * * *